(12) United States Patent
Fomovskaia et al.

(10) Patent No.: US 6,746,841 B1
(45) Date of Patent: Jun. 8, 2004

(54) FTA- COATED MEDIA FOR USE AS A MOLECULAR DIAGNOSTIC TOOL

(75) Inventors: Galina Fomovskaia, Ann Arbor, MI (US); Martin Alexander Smith, Rockland, MA (US); James Critser Davis, Rockland, MA (US); Kevin Jones, Kent (GB); Mikhail A. Fomovsky, Newton, MA (US)

(73) Assignee: Whatman Inc., Newton, MA (US)

( * ) Notice: Subject to any disclaimer, the term of this patent is extended or adjusted under 35 U.S.C. 154(b) by 72 days.

(21) Appl. No.: 09/736,659

(22) Filed: Dec. 14, 2000

Related U.S. Application Data (63) Continuation-in-part of application No. PCT/US00/10230, filed on Apr. 14, 2000.
(60) Provisional application No. 60/193,556, filed on Mar. 31, 2000, provisional application No. 60/180,353, filed on Feb. 4, 2000, and provisional application No. 60/129,191, filed on Apr. 14, 1999.

(51) Int. Cl.$^7$ .......................... C12Q 1/68; G01N 33/543
(52) U.S. Cl. .......................... 435/6; 435/7.91; 435/7.92
(58) Field of Search ............................. 435/6, 2, 7.92, 435/91.1; 422/57; 424/488; 536/25.4, 23.1

(56) References Cited

U.S. PATENT DOCUMENTS

| | | | | |
|---|---|---|---|---|
| 5,234,809 | A | * 8/1993 | Boom et al. | ................ 435/91.2 |
| 5,496,562 | A | 3/1996 | Burgoyne | ................... 424/488 |
| 5,756,126 | A | * 5/1998 | Burgoyne | |
| 5,807,527 | A | 9/1998 | Burgoyne | ................... 422/488 |

FOREIGN PATENT DOCUMENTS

| | | | |
|---|---|---|---|
| WO | WO 00/04195 | 1/2000 | ............ C12Q/1/70 |
| WO | WO 00/53807 | 9/2000 | ............ C12Q/1/68 |
| WO | WO 00/62023 | 10/2000 | ............. G01J/1/48 |

OTHER PUBLICATIONS

Esienberg, et al., "High throughput automated DNA sample analysis for both RFLP ans PCR using FTA . . . ", http://www.bio.flinders.edu.au/eisenb.html, Date of print–out: Feb. 24, 1999.*

Yang, et al., "DNA ligands that bind tightly and selectively to cellobiose," *Proc. Natl. acad. Sci. USA* vol. 95, pp. 5462–5467, May 1998.

Rogers, et al., "Reverse transcription of an RNA genome from databasing paper (FTA®)," Biotechno Appl. Biochem. (2000) vol. 31, pp. 219–224.

Eisenberg, et al., "High throughput automated DNA sample analysis for both RFLP and PCR using FTA<® paper and the Rosys robotic microplate processor," http://www.bio.flinders.edu.au/eisenb.html, Date of print–out: Feb. 24, 1999.

Both, et al., "FTA Paper, DNA, Time and the Profiler," http://www.bio.flinders.edu.au/vidocq.html Date of print–out: Feb. 22, 1999.

Renz, et al., "A colorimetric method for DNA hybridization," Nucleic Acids Research, vol. 12, No. 8 1984, pp. 3435–3444.

Del Rio, et al., "Reusing the Same Blood–stained Punch for Sequential DNA Amplifications and Typing," BioTechniques, vol. 20, No. 6, (1996), pp. 970–974 (pp. 971 & 973 are blank pages).

Matsuhisa, et al., "A Simple Staining Method for DNA and RNA Blotted on a Membrane Using a Polyethylene-imine–Enzyme Conjugate," J. Biochem., vol. 116, pp. 478–481, (1994).

* cited by examiner

*Primary Examiner*—Kenneth R. Horlick
*Assistant Examiner*—Cynthia Wilder
(74) *Attorney, Agent, or Firm*—Edwards & Angell, LLP (57) ABSTRACT

There is provided a substrate for lysing calls and purifying nucleic acid having a matrix and a coating and an integrity maintainer for maintaining the purified nucleic acid. Also provided is a method of purifying nucleic acid by applying a nucleic acid sample to a substrate having an anionic detergent affixed to a matrix, the substrate physically capturing the nucleic acid, bonding the nucleic acid to a substrate and generating a signal when the nucleic acid bonds to the substrate indicating the presence of the nucleic acid. A kit for purifying nucleic acid containing a coated matrix and an integrity maintenance provider for preserving the matrix and purifying nucleic acid is also provided.

13 Claims, 4 Drawing Sheets

FTA- COATED MEDIA FOR USE AS A MOLECULAR DIAGNOSTIC TOOL

CROSS-REFERENCE TO RELATED APPLICATIONS

This is a Continuation-in-part of PCT application No. PCT/US00/10230, filed Apr. 14, 2000, which claims the benefit of priority under 35 USC Section 119(e) of U.S. Provisional Patent Application No. 60/129,191, filed on Apr. 14, 1999; U.S. Provisional Patent Application No. 60/180,353, filed on Feb. 4, 2000; and U.S. Provisional Patent Application No. 60/193,556, filed on Mar. 31, 2000, all of which are incorporated herein by reference.

TECHNICAL FIELD

The present invention relates to an apparatus, media, and method for DNA evaluation.

BACKGROUND ART

Genotyping is the discipline of identifying an individual's genome in relation to disease specific alleles and/or mutations that occur as an effect of parental linkage. The rapid purification of human genomic DNA is an essential part of a genotyping process; the genomic DNA of an individual being the structural unit for the entire DNA sequence of every allele expressed.

Human genomic DNA cannot be directly sequenced. In order to carry out sequence analysis on regions of the chromosomes that may contain portions of mutation or disease specific sequences, selected portions are amplified via PCR and the amplified products are sequenced. The selected portions of the chromosomes that are amplified are dictated by the specific sequence of the primers used in the PCR amplification. The primer sets that are used in genotyping studies are commercially available and are representative for the chromosome under examination. If linkage studies identify that a disease bearing sequence is on a particular chromosome, then many primer sets will be utilized across that chromosome in order to obtain genetic material for sequencing. The resultant PCR products may well represent the entire chromosome under examination. Due to the large length of chromosomes, many PCR reactions are carried out on the genomic DNA template from a single patient.

Human genomic DNA is purified by a variety of methods (Molecular Cloning, Sambrook et al. (1989)). Consequently, many commercial kit manufacturers provide products for such techniques, for example: AmpReady™ (Promega, Madison, Wis.), DNeasy™ (Qiagen, Valencia, Calif.), and Split Second™ (Roche Molecular Biochemicals, Indianapolis, Ind.). These products rely on the use of specialized matrices or buffer systems for the rapid isolation of the genomic DNA molecule.

More recently, microporous filter-based techniques have surfaced as tools for the purification of genomic DNA as well as a whole multitude of nucleic acids. The advantage of filter-based matrices are that they can be fashioned into many formats that include tubes, spin tubes, sheets, and microwell plates. Microporous filter membranes as purification support matrices have other advantages within the art. They provide a compact, easy to manipulate system allowing for the capture of the desired molecule and the removal of unwanted components in a fluid phase at higher throughput and faster processing times than possible with column chromatography. This is due to the fast diffusion rates possible on filter membranes.

Nucleic acid molecules have been captured on filter membranes, generally either through simple adsorption or through a chemical reaction between complementary reactive groups present on the filter membrane or on a filter-bound ligand resulting in the formation of a covalent bond between the ligand and the desired nucleic acid.

Porous filter membrane materials used for non-covalent nucleic acid immobilization have included materials such as nylon, nitrocellulose, hydrophobic polyvinylidinefluoride (PVDF), and glass microfiber. A number of methods and reagents have also been developed to also allow the direct coupling of nucleic acids onto solid supports, such as oligonucleotides and primers (eg. J. M. Coull et al., Tetrahedron Lett. Vol. 27, page 3991; B. A. Conolly, Nucleic Acids Res., vol. 15, page 3131, 1987; B. A. Conolly and P. Rider, Nucleic Acids Res., vol. 12, page 4485, 1985; Yang et al P.N.A.S. Vol.95: 5462–5467). UV cross-linking of DNA (Church et al., PNAS, vol. 81, page 1991, 1984), The Generation Capture Column Kit (Gentra Systems, Minneapolis, Minn.) and RNA (Khandjian, et al., Anal. Biochem, Vol. 159, pages 227, 1986) to nylon membranes have also been reported.

Many chemical methods have been utilized for the immobilization of molecules such as nucleic acids on filter membranes. For example, activated paper (TransBind.TM, Schleicher & Schuell Ltd., Keene, N.H.) carbodimidazole-activated hydrogel-coated PVDF membrane (Immobilin-IAV.TM, Millipore Corp., Bedford, Mass.), MAP paper (Amersham, Littlechalfont Bucks, Wis.), activated nylon (BioDyne. TM, Pall Corp., (Glen Cove, N.Y.), DVS- and cyanogen bromide-activated nitrocellulose. Membranes bound with specific ligands are also known such as the SAM2TM Biotin Capture Membrane (Promega) which binds biotinylated molecules based on their affinity to streptavidin or MAC affinity membrane system (protein A/G) (Amicon, Bedford, Mass.). Some of the disadvantages of covalent attachment of biomolecules onto activated membranes are:

a) Molecule immobilization is often slow requiring 20–180 minutes for reaction completion.

b) High ligand and biomolecule concentration is needed for fast immobilization.

c) Constant agitation is needed during the immobilization process that may result in biomolecule denaturation and deactivation.

d) Once the immobilization process is complete, often a blocking (capping) step is required to remove residual covalent binding capacity.

e) Covalently bound molecules can not be retrieved from the filter membrane.

There is a need in various specific areas, such as forensics, for a nucleic acid immobilization media and procedure that exhibits the high specificity of covalent immobilization onto the filter membrane without the use of harsh chemical reactions and long incubation times, which can also be used at crime scenes, with blood sample archiving and other related uses. In particular there is a need for the capture and separation of nucleic acids from a mixture in a fluid phase onto a filter membrane matrix in forensics. Of special interest is the ability to store or archive the bound nucleic acids on the filter membrane matrix for such uses.

More recently, glass microfiber, has been shown to specifically bind nucleic acids from a variety of nucleic acid containing sources very effectively (for example see: Itoh et al (1997) Simple and rapid preparation of plasmid template by filtration method using microtiter filter plates. NAR, vol.

25, No. 6: 1315–1316; Andersson, B. et al (1996) Method for 96-well M13 DNA template preparations for large-scale sequencing. BioTechniques vol. 20: 1022–1027). Under the correct salt and buffering conditions, nucleic acids will bind to glass or silica with high specificity.

Based on U.S. Pat. Nos. 5,496,562, 5,756,126, and 5,807,527, it has been demonstrated that nucleic acids or genetic material can be immobilized to a cellulosic-based dry solid support or filter (FTA filter). The solid support described is conditioned with a chemical composition that is capable of carrying out several functions: (i) lyse intact cellular material upon contact, releasing genetic material, (ii) enable and allow for the conditions that facilitate genetic material immobilization to the solid support (probably by a combination of mechanical and chaotrophic), (iii) maintain the immobilized genetic material in a stable state without damage due to degradation, endonuclease activity, UV interference, and microbial attack, and (iv) maintain the genetic material as a support-bound molecule that is not removed from the solid support during any down stream processing (as demonstrated by Del Rio et al (1995) Bio-Techniques. Vol. 20: 970–974).

The usefulness of the so called FTA cellulosic filter material described in U.S. Pat. Nos. 5,496,562, 5,756,126, and 5,807,527 has been illustrated for several nucleic acid techniques such as bacterial ribotyping (Rogers, C & Burgoyne, L (1997) Anal. Biochem. Vol. 247: 223–227), detection of single base differences in viral and human DNA (Ibrahim et al (1998) Anal. Chem. Vol. 70: 2013–2017), DNA databasing (Ledray et al (1997) J. Emergency Nursing. Vol.23, No. 2: 156–158), automated processing for STR electrophoresis (Belgrader, B & Marino, M (1996) L.R.A. vol.9: 3–7, Belgrader et al (1995) BioTechniques. Vol. 19, No. 3: 427–432), and oligonucleotide ligation assay for diagnostics (Baron et al (1996) Nature Biotech. Vol 14: 1279–1282).

It has been shown that nucleic acid or genetic material applied to, and immobilized to, FTA filters cannot be simply removed, or eluted from the solid support once bound (Del Rio et al (1995) BioTechniques. Vol. 20: 970–974). This is a major disadvantage for applications where several downstream processes are required from the same sample, such a STR profiling and genotyping.

Currently, cellular material is applied to FTA filter media, and generally the cellular material, once applied forms a spot on the FTA filter. From this spot, small punches can be taken; each small punch will have immobilized to it enough nucleic acid or genetic material to facilitate a single downstream process such as a PCR reaction. As the two primers administered to a PCR reaction are presented in solution, it is of no consequence that the cellular nucleic acid template is immobilized to the filter. All amplicon will be formed in solution. Amplicon can then be readily removed from the reaction by aspirating the liquid phase away from the FTA solid filter punch. Therefore, for multiple processing from a single sample, many punches have to be taken. Multiple punching is very time consuming, and as yet, has not lent itself to simplified automation.

It is much more desirable to provide nucleic acid as a soluble fraction from which aliquots can be readily dispensed to as many reactions as required. Automated liquid handling of this type is a fundamental technique within the pharmaceutical and other industries (for example see: Armstrong et al (1998) J. Biomolecular Screening. Vol. 3, No. 4: 271–275).

It is desirable to adapt the present technology and modify it for specific use in the forensic art Additionally, it would be advantageous to be able to rapidly qualify and quantify nucleic acid on media, either in correlation with such uses, or independent thereof.

SUMMARY OF THE INVENTION

According to the present invention there is provided a substrate for lysing cells and purifying nucleic acid having a matrix and a coating and an integrity maintainer for maintaining the purified nucleic acid. Also provided is a method of purifying nucleic acid by applying a nucleic acid sample to a substrate, the substrate physically capturing the nucleic acid, bonding the nucleic acid to the substrate and generating a signal when the nucleic acid bonds to the substrate indicating the presence of the nucleic acid. A kit for purifying nucleic acid containing a coated matrix and an integrity maintenance provider for preserving the matrix and purifying nucleic acid is also provided.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE INVENTION

The present invention most generally provides a medium for storage and subsequent analysis of the genetic material, the medium including a matrix for immobilizing a genetic material thereon and allowing subsequent elution of the genetic material therefrom and an integrity maintenance provider for preserving the matrix. A coating is functionally associated with the matrix for enabling cellular lysis and releasing the genetic material from the lysed cells awhile stabilizing the immobilized released genetic material. A method is also provided of storing a genetic material most generally including the steps of immobilizing a genetic material on the matrix which allows subsequent elution of the genetic material and lysing calls and releasing the genetic material from the lysed cells while stabilizing the immobilized released genetic material and, an indicator capable of generating a signal when the nucleic acid bonds to the substrate. The genetic material can then be analyzed in solution as opposed to being immobilized on the matrix. The present invention is well suited for various novel uses of the technology. More specifically, the present invention provides a product able to (1) identify the presence of nucleic acid on a substrate and do so rapidly; (2) maintain the integrity of the substrate; and (3) be used in novel embodiments which take advantage of these improvements.

The chemical composition of the substrate facilitates the lysis of whole cells and the subsequent capture of the released nucleic acids. The chemical composition further aids in their long term storage. The composition of the substrate is such that the rapid purification of the captured nucleic acid can be carried out. That is, the substrate itself allows for the release of nucleic acid by an elution step thereby providing a soluble nucleic acid fraction. As discussed in more detail below and exemplified in the following examples, the present invention is most efficient with regard to elution of total DNA from the sample. However, nucleic acid and nucleic acid populations can be specifically eluted.

The substrate, when processed in accordance with the invention to provide a nucleic acid eluting filter material provides a number of advantages and applications. Thus, use of the substrate of the present invention provides advantages of identification and quantification of nucleic acid-containing biological fluids as well as multiple processing of fluids.

Figure 1:
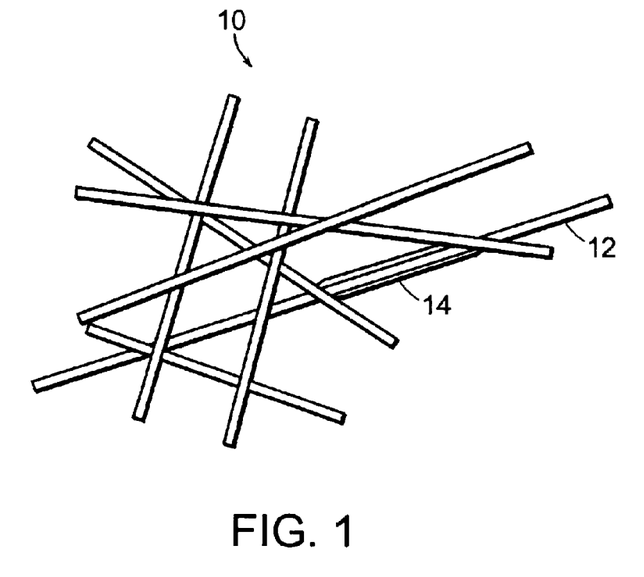
FIG. 1 is a cross-sectional view of a filter membrane made in accordance with the present invention.
Figure 2:
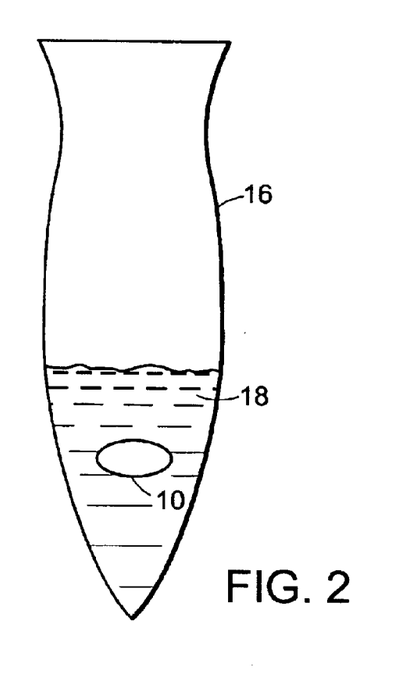
FIG. 2 is a cross-section of a device made in accordance with the present invention.

The present invention, generally shown at 10 in FIG. 1, includes the following components:

(i) a suitable matrix, preferably a filter membrane 12;

(ii) a chemical coating 14; and (iii) an integrity maintenance provider.

Reaction of the filter membrane with the chemical coating solution produces the filter membrane of the invention. If the membrane is fibrous, this coating is a coating of the filter fibers, not the filter surface. Alternatively, the coating can impregnate the fibers.

Preferably, the matrix of the present invention is a porous material in the form of a filter membrane.

The term "filter membrane" or "matrix" as used herein means a porous material or filter media formed, either fully or partly from glass, silica or quartz including their fibers or derivatives thereof, but is not limited to such materials. Other materials from which the filter membrane can be composed also include cellulose-based (nitrocellulose or carboxymethylcellulose papers), hydrophilic polymers including synthetic hydrophilic polymers (eg. polyester, polyamide, carbohydrate polymers), polytetrafluoroethylene, and porous ceramics.

The media used for the filter membrane of the invention includes any material that does not inhibit the sorption of the chemical coating solution and which does not inhibit the storage, elution and subsequent analysis of nucleic acid-containing material added to it. This includes flat dry matrices or a matrix combined with a binder. It is preferred that the filter membrane of the invention be of a porous nature to facilitate immobilization of nucleic acid. Unlike prior art supports, the support of the present invention allows for elution of the genetic material therefrom in a state that allows for subsequent analysis. Unexpectedly, such elution is a time efficient step thereby providing for almost immediate analysis.

The term "chemical coating solution" as used herein means a chemical composition that is able to sorb to the aforementioned filter membrane. The composition of the chemical coating solution is as described and relates to that outlined in U.S. Pat. Nos. 5,756,126, 5,807,527, and 5,496,562. Adsorption of the chemical coating solution to the selected filter membrane results in the formation of the filter membrane of the invention.

More specifically, the chemical coating solution includes a protein denaturing agent and a free radical trap. The denaturing reagent can be a surfactant that will denature proteins and the majority of any pathogenic organisms in the sample. Anionic detergents are examples of such denaturing reagents. The chemical solution can include a weak base, a chelating agent, and the anionic surfactant or detergent, and optionally uric acid and urate salt as discussed in detail in the above-cited U.S. Pat. No. 5,807,527. More preferably, the sneak base can be a Tris, trishydroxymethyl methane, either as a free base or as the carbonate, and the chelating agent can be EDTA, and the anionic detergent can be sodium dodecyl sulfate. Other coatings having similar function can also be utilized in accordance with the present invention.

Alternatively, the substrate consists of a matrix and an anionic detergent affixed thereto. The anionic detergent can be selected from the group including sodium dodecyl sulfate (SDS). SDS can be obtained in various forms, such as the $C_{12}$ form and the lauryl sulfate. Other anionic detergents can be used, such as alky aryl sulphonates, sodium tetradecyl-sulphate long chain (fatty) alcohol sulphates, sodium 2-ethylhexysulphate olefine sulphates, sulphosuccinates or phospate esters. The anionic detergent, such as the SDS, can be applied to the filter matrix at varying concentrations.

Generally, 5%–10% SOS can be used in accordance with the present invention. For example, increased concentrations of SDS, up to 10%, which cannot be accommodated within an FTA cocktail, as set forth in the prior art patents discussed above, provided greater critical micelle concentration which generates greater lysing capability and thus greater yield of target nucleic acid, as demonstrated in the example section set forth below. A definite optimum SDS concentration is achieved in the 5–7.5% SDS concentration range for coating particular glass microfiber in order to enrich for and purify different plasmid populations directly from liquid cultures in a multi-well format, such formats being well known in the art.

The term "functionally associated with" means that the coating is disposed, sorbed, or otherwise associated with the support of the present invention such that the support and coating function together to immobilize nucleic acid thereon through an action of cellular lysis of cells presented to the support. That is, the coating can be adsorbed, absorbed, coated over, or otherwise disposed in functional relationship with the media. For example, the support, in the form of a filter membrane, can be disposed in a solution containing the chemical solution. As stated above, the support of the present invention is preferably a porous filter media and can be in the form of a flat, dry media. The media can be combined with a binder, examples of binders well-known in the art being polyvinylacrylamide, polyvinylacrylate, polyvinylalcohol, gelatin, for example.

The matrix of the present invention can be capable of releasing the genetic material immobilized thereto by a heat elution. Preferably, such a heat elution is accomplished by the exposure of the support having the genetic material stored thereon to heated water, the water being nuclease free. This capacity to allow for elution characterizes the various support materials of the present invention.

The filter membrane of the invention is such that at any point during a storage regime, it allows for the rapid purification of immobilized nucleic acid. The invention is such that immobilized nucleic acid is collected in the form of a soluble fraction following a simplified elution process, during which immobilized nucleic acid is released from the filter membrane of the invention. The filter membrane of the invention yields nucleic acid of sufficient quality that it does not impair downstream analyses such as polymerase chain reaction (PCR), ligase chain reaction (LCR), transcription mediated amplification (TMA), reverse transcriptase initiated PCR, DNA or RNA hybridization techniques, sequencing, and the like.

Nucleic acid immobilization to a solid support, although a suitable template for singular PCR reactions, cannot be measured or detected by traditional techniques such as optical density or fluorescence. Nucleic acid must be in solution for these techniques. Other post-purification techniques wherein nucleic acid is desired in the soluble form includes cloning, hybridization protection assay, bacterial transformation, mammalian transfection, transcription-mediated amplification, and other such methods. The present invention provides nucleic acid in such a soluble form. Additionally, the signal generated by the indicator of the present invention provides positive identification of the presence of nucleic acid on the substrate.

The source of the nucleic acid can be a biological sample containing whole cells. The whole cell can be, but not restricted to, blood, bacterial culture, bacterial colonies, saliva, urine, drinking water, plasma, stool samples, and sputum. The samples can be collected by various means known in the art, transported to the substrate, and then applied thereto. Alternatively, the substrate can be in the form of a sampling device, such as a swab, sheet material, ball, or the like and the sample can be obtained directly from the source. In other words, the substrate can be in the form of a device which can swipe or otherwise obtain the cell sample from a source. The source can be a sample tube containing a liquid sample, an organ, such as a mouth, ear, or other part of a human or animal, a sample pool, such as a blood sample at a crime scene or the like, or other various sources of cells known in the scientific, forensic, and other arts.

Additionally, the fibrous filter matrix of the present invention can be manufactured in various forms. For example, the fibrous filter matrix can be manufactured in a sheet form, which allows for it to be in various formats such as multi-well plates, spin tubes, slides, cartridges, swabs, and pads.

The term "integrity maintainer" or "integrity maintenance means" as used herein means a sealable member that prevents degradation afar loss of the matrix. Preferably, the integrity maintainer of the present invention creates an air tight seal thus preventing air, bacteria or other contaminants from coming into contact, with the matrix and purified nucleic acid. The integrity maintainer can be in the form of a plastic bag, with or without a seal, cellophane, a sealable container, parafilm and the like.

The integrity maintainer can open to allow application of a sample onto the matrix. It is then closed and sealed thereby containing the substrates. Accordingly, if the substrate ages and becomes brittle, it is contained and not lost. Alternatively, the integrity maintainer can be applied over the substrate after the sample is applied.

The present invention provides a method for isolating and archiving nucleic acid by the general steps of applying a nucleic acid sample to a substrate consisting of the coating fixed to the matrix, the substrate physically capturing the nucleic acid, and then bonding the nucleic acid to the substrate. Then a signal is generated when the nucleic acid bonds to the substrate. The bonding step is achieved by heating the substrate having nucleic acid applied thereto, by the method discussed above.

The applying step can be achieved by applying whole cells to the substrate. The substrate itself actually induces the lysing of the cells thereby releasing the nucleic acid into the substrate. By being a porous substrate, the substrate presents a vast surface area upon which the nucleic acid is bound.

A washing step, such as with various buffers set forth in the example section, but not limited thereto, can be achieved and is done after cell lysis. The substrate then physically captures the nucleic acid within the intrastaces thereof.

The bound nucleic acid can be released from the substrate for further processing and analysis. The release is achieved by washing steps at elevated temperature, as demonstrated in the examples below. Unexpectedly, enrichment for different populations of nucleic acid from the same cell source can be achieved using incremental temperature regimes, For example, plasma DNA can be isolated and enriched from bacterial colonies using the substrate of the present invention. Populations, such as larger populations of supercoiled plasmid, followed by nicked plasmid and finally by linear plasmid migrating to the top of the isolating gel can be achieved utilizing incremental increases in incubation temperature.

It is known that the FTA coating cocktail of the prior art contains 2% SDS. It is unlikely that this percentage can be increased due to saturation points when in conjunction with other components of the cocktail. This limits the lysing capability of the FTA coating filters of the prior art as a critical micelle concentration of SDS can be easily reached when presented with large numbers of cells, such as with a bacterial colony. Therefore, substrates containing a greater concentration of the lytic agent, the anionic detergent, enable greater lysing capability and in turn, greater nucleic acid recoveries. This is demonstrated in the examples set forth below.

The filter membrane of the invention can possess the same chemical component as FTA that enables the action of cellular lysis and nucleic acid release upon sample application. The chemical component ensures nucleic acid stability via protein denaturants, a free radical trap, and viral/microbial inhibitors. The difference between prior art FTA solid supports and the filter membrane of the invention is that the base solid support, or filter, has been changed compared to that described for FTA products. This change in solid support material, or filter, has enabled, upon a simplified heat elution step, bound nucleic acid to be removed from the filter membrane of the invention whereas it cannot be removed from FTA solid support (see Del Rio et al (1995) BioTechniques. Vol. 20: 970–974). The nucleic acid released from the filter membrane of the invention is thus presented as a soluble fraction that can be readily aliquoted to multiple downstream processes such as PCR amplification. The eluted soluble nucleic acid can also be entered into techniques where soluble nucleic acid is a necessity such as optical density analysis, fluorescence detection, cloning, transformation, and the like. This added technique of elution enables high throughput multiple processing regimes, such as genotyping.

The present invention can find utility in many areas of genomics. For example, the present invention provides the capability to elute bound genetic material for the rapid purification of the genetic material to be utilized in any number of forensic applications, such as identification, paternity/maternity identification, and at the scene of a crime.

Prisoners from many countries are required to give a genetic sample (blood or buccal sample) for DNA fingerprinting purposes. The use of the present invention provides a means for the long term storage of prisoner genetic material. If necessary, the genetic material can be tested as soon as it is taken or many years after storage. The genetic material can be obtained as either a soluble or solid phase fraction once isolated on the filter media of the present invention.

The present invention can be utilized for paternity/maternity identification having a particular use for a mother or hospital wherein a newborn has been mislaid in the hospital. The rapid ability of the present invention to provide for a purified genetic sample provides even greater utility in such instances where a speedy identification of a mislaid child would be most propitious.

The present invention is a significant contribution to current methodology for the preparation of soluble genetic material which are otherwise time consuming and often result in inadequate template that is damaged or contaminated. The present invention provides high yield of purified genetic material of superior quality in less than twenty minutes of laboratory time. The rapidly purified genetic material can be utilized for any number of food/agricultural applications such as tracing, breeding, identification, and cloning.

The efficiency with which food manufacturers detect pathogenic outbreak in both their livestock and finished product is the measure of a successful company. The use of the present invention as a swab that can be simply pressed against food or the use of a card onto which carcass blood can be spotted enables uses of the present invention to rapidly isolate and detect for the presence of pathogenic genetic material. Time consuming prior art assay techniques and involved nucleic acid preparations do not need to be performed if the present invention is utilized. Collected pathogenic nucleic acid can be used as a soluble fraction or solid phase fraction with the choice of an elution step.

Tracing carcass material, whether for legal or health issues, enables manufacturers to keep control of their products. At the point of kill in a slaughter house, a card utilizing the present invention can be attached to the carcass onto which its blood has been spotted. At the same time, a second card can be spotted with the same blood and kept as an archive at the slaughter house. If an identification issue arises for a certain carcass, genetic records on both the carcass and the slaughterhouse can be utilized. If the carcass card is inadvertently removed, identification can still be carried out by simply pressing a carcass flesh onto such a card.

Identifying the desired genes and characteristics that are required for a subsequent generation of a plant or animal requires the time effective and reliable generation of nucleic acid from potential parents. The present invention can be used for the isolation of either soluble or solid phase genetic material to provide effective and reliable results in such a need. Likewise, the present invention, in the form of microplates, a tube or a chip, can be used for the generation and detection of genetic material. The present invention provides methodology for superior template preparation time (whether soluble or solid) and cost effective archiving.

Pressing a media, in the form of a swab or otherwise, enables the user to pick up any contaminated microbes on food products of any type. Genetic material isolated from the media can then be utilized for any manner of diagnostic procedure depending on whether soluble or solid phase genetic material is required. This analysis can be done almost effectively immediately, as opposed to prior art techniques.

By the use of genetic manipulation techniques, food stuff has been produced with increased size, flavor, ripening, and sugar content. Many countries prohibit the sale of genetically modified food products and therefore require testing to be carried out. Since one is looking for specific genes that generate these characteristics, genetic material is required. The present invention can be used to provide rapid purification of both soluble and solid phase genetic material.

In view of the above, the present invention finds utility in various areas of genomics.

Initial experiments were performed to demonstrate the possibility of utilizing FTA-coated materials such as membranes for the quantitation and detection of DNA. First experiments illustrated that whole cells can be deposited onto FTA-coated membrane such as cellulose nitrate, with cell lysis and nucleic acid binding readily carried out on contact. Immobilized DNA can be detected (and quantified) by the use of a specific and non-specific DNA probe or other signal generators and one of the versions of immunoassay.

The use of an FTA coated substrate onto which suspected leukodepleted blood is spotted. The nucleic acid component of the sample is affixed to the substrate and is available for direct measurement with a probe such as PEI. If detection is below a set lower limit then the sample is deemed leukodepleted. Such a system offers great timesaving for blood banks that currently use microscopy for characterizing depletion efficiencies. With a trend more towards leukodepletion of blood at the source rather than bedside, a simple detection methodology is very useful.

There are many liquids in several industries that should not have any biocontamination at point of sale. Also liquids are monitored for increase in biocontamination over time. Liquids may also include biological samples where the presence of microbes may illustrate disease or infection. A sample of a liquid would be added to an FTA coated substrate, cells within the sample, including unwanted bioload, will lyse on contact with nucleic acid fixing instantly. Direct detection with either a general DNA probe, to show the presence of cellular contamination, can be used, or a species specific probe can be employed, and by hybridization identify the presence of unwanted cells from a multicellular sample. This type of system can be utilized in the food industry, with liquids including milk, wine, beer, and juices. In medicine, urine, blood, and stool extract can all be applied to the system with direct detection of the immobilized nucleic acid carried out with species-specific probes. In the environmental industry drinking water, seawater, and river water can find utility within the proposed system.

A disease such as lupus is characterized by the presence of double stranded DNA in the bloodstream. A sufferer of lupus will therefore have in their system antibodies that will have been raised to the presence of the dsDNA antigen. Human dsDNA spotted and fixed to FTA coated membrane can therefore be utilized as a platform for carrying out direct ELISA if the applied sample contains the lupus antibodies. Lengthy immobilization steps in order to carry cut "traditional" ELISA are negated with an FTA approach.

A detailed description of the FTA-coated material and methods of using the media is set forth in the Examples and accompanying figures included herewith and incorporated by reference in its entirety.

EXAMPLES

Example 1

Human white blood cells and purified DNA were used as samples to load onto pieces of FTA-treated membrane for an ELISA assay based on the ionic interaction between polyethyleneimine-peroxidase conjugate (PEI-PO) and DNA.

The goal of the experiment was to confirm that DNA could be attached to the FTA membrane for subsequent detection and to confirm that DNA could be released from the cell and attached to a membrane firmly enough for following detection.

Materials and Protocol

Four membranes were utilized. The membranes are as follows: 1. Nitrocellulose membrane, pore size 0.2 µm, Schleicher & Schull; 2. Nylon membrane, pore size 0.2 µm, Osmonics; 3. Nylon membrane, pore size 1.2 µm, Osmonics; and 4. FTA-glass, grade F572-08, Whatman (used for comparison).

The membranes were soaked with the FTA colution for two hours at room temperature with gentle agitation, dried completely at room temperature, and baked at 80° C. for one hour.

DNA samples of WBC at $5 \times 10^3$ cel/µl, WBC, 5 cells/µl, and DNA, 2 µg/µl were used.

Protocol:

All assay steps were performed in one 96 well plate. The circles of each membrane, 0.5 mm in diameter, were put on the bottom of the wells. DNA samples of 3 µl per well were loaded, in duplicate. Then the plate was subsequently blocked with PBS/BSA/Twin-20 solution, incubated with a Polyethyleneimine-Peroxidaze conjugate, washed with PBS/BSA/Twin-20 solution, and finally incubated with different substrates for Peroxidase to develop colored soluble or insoluble products.

Figure 3:
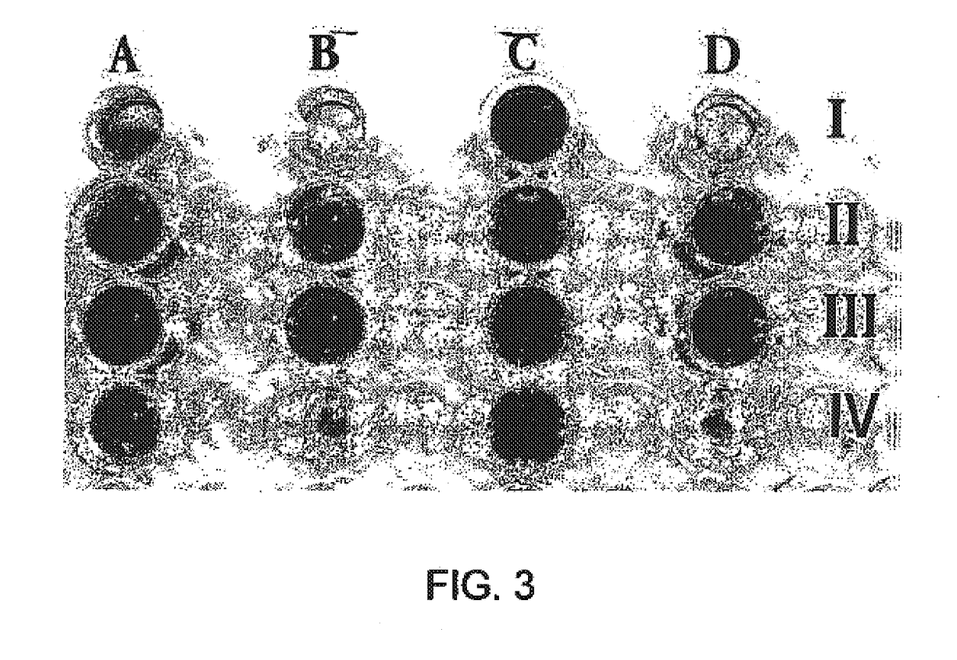
FIG. 3 is a photograph showing the color intensity of the soluble product developed on the DNA samples loaded on the FTA-membrane by polyethyleneimide-peroxidase conjugate assay.

Results:

DNA-positive and DNA-negative samples developed different color intensities on the FTA-nylon, and FTA-nitrocellulose membranes, both having a pore size of 0.2 µm, when the result of the enzyme reaction was soluble products (table 1, FIG. 3).

Figure 4:
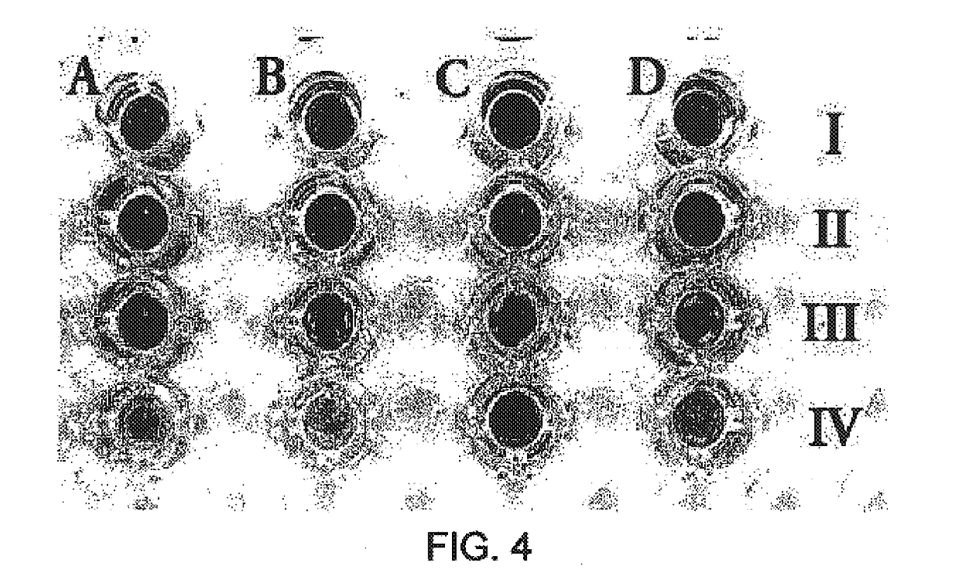
FIG. 4 is a photograph showing the color intensity of the insoluble product developed on the DNA samples loading on the FTA-membrane by polyethyleneimide-peroxidase conjugate assay.

DNA-positive and DNA-negative samples only developed different color intensity, on FTA-nitrocellulose membrane, with a pore size of 0.2 µm, when the result of the enzyme reaction was insoluble product (table 2, FIG. 4).

Advantages or Unexpected Features

DNA can be loaded on the FTA or SDS treated membrane for later use in an ELISA determination. Additionally, DNA can be released from WBA on FTA treated membrane (0.2 µm pore size) for subsequent analytical determinations.

Physical and chemical properties of the FTA-treated membrane (such as pore size or membrane composition) are critical for their application for DNA evaluation. For example, FTA-nylon membrane, 0.2 µm pore size, showed the best results for measuring a differing amount of DNA and discriminating the DNA-positive and DNA-negative samples.

Color Intensity Developed on the Samples Loaded on the FTA Materials by PEI-PO Assay With the Soluble Product of PO, Reading at 490 nm, Jan. 13, 2000 Test background with no ring developed when adding $5 \times 10$ WBC/µl. When 2 µg/µl DNA was added the 2 µm Nylon developed a dark brown background. Finally, a light brown background developed in the control situation.

1.2 µm Nylon

For all of the above concentrations, the background of all pieces is the same dark brown. There is no difference in the color of the DNA-positive membranes and the control one.

FTA-glass

As with the 1.2 µm nylon material, the background of all pieces is the same dark brown. There is no difference in the color of the DNA-positive membranes and the control one.

0.2 µm Nitrocellulose

With the addition of $5 \times 10^3$ WBC/µl a dark brown ring developed in the middle of the membrane with a very light background A very light brown ring in the middle of the membrane developed when $5 \times 10$ WBC/µl was added. A dark brown background developed when 2 µl/µl DNA was added. A very light brown background developed in the control situation.

Example 2

FTA Cellulose Nitrate Membrane Application for DNA Determination

Membranes

Whatman Cellulose Nitrate Membranes having pore sizes of 0.1, 0.2, 0, 45, and 0.8 µm were used for the following experiments. The Membranes were soaked with the FTA solution for one hour at 80° C. with gentle agitation, dried completely at room temperature, and baked at 80° C. for one hour.

DNA Samples

Three DNA samples were used for the following experiments. These samples include the following: 1. Single-stranded DNA, 1 µg/µl; 2. Single-stranded DNA, 0.2 µg/µl; and 3. DNA-negative sample—PBS with 3% BSA solution.

Protocol

2 µl of the single stranded DNA solutions having a DNA concentration of 1 µg/µl and 0.2 µg/µl were fixed on the pieces of the membrane in a 96 well plate. The plate was blocked with PBS-BSA-Twin-20 buffer solution, incubated with a polyethyleneimine-peroxidate (PEI-PO) conjugate and washed three times before incubation with substrate solutions.

DNA attached to the FTA membrane, in one set of the wells, was visualized directly on the membrane when he insoluble product of PO was developed subsequent to incubaton with 3,3'-dianisidine. A duplicate set of the wells was

|     |                      | A<br>$5 \times 10^3$ WBC/µl | B<br>$5 \times 10$ WBC/µl | C<br>2 µg/µl DNA | D<br>0-control |
|-----|----------------------|----------|----------|--------------|--------------|
| I   | 0.2 µm nylon         | 1.131    | 0.58     | over reading | 0.511        |
| II  | 1.2 µm nylon         | 2.279    | 1.445    | 1.92         | 2.408        |
| III | FTA-glass            | over reading | over reading | over reading | over reading |
| IV  | 0.2 µm nitrocellulose| 1.034    | 0.506    | 2.208        | 0.327        |

Over reading occurs when an optical density of the sample is more than 3,000. A 3 µl sample was loaded into each well.

Visual Estimation of the Color Development on the Samples Loaded on FTA-materials by PEI-PO Assay With the Insoluble Product of PO, Jan. 13, 2000, Test 0.2 µm Nylon A dark brown ring developed in the middle of the membrane when treated with $5 \times 10^3$ WBC/µl. A light brown incubated with 1,2-ortophenylenediamine dihydrochloride (OPD) and color development in supernatant was estimated at 490 nm.

Results

The color intensity that was developed on the FTA membrane directly correlates with the amount of DNA loaded per well. The best resolution between DNA-positive samples with different DNA concentration and DNA-negative samples was achieved on the membrane with 0.8 μm pore size, the reading at 490 μm was: DNA negative wells, 0.204; 0.2 μg DNA/well, 1.070; 1 μg DNA/well, 1.776.

When the insoluble PO product indicated the amount of DNA, the most distinct differences between DNA-positive samples with different DNA concentration and DNA-negative samples was achieved on the membrane with 0.1 μm pore size.

Example 3

FTA Nylon and Nitrocellulose Membrane Application for WBA Determination

Membranes

Four membranes were used for the following experiment. These membranes are as follows: Nitrocellulose membrane, pore size 0.2 μm, Schleicher & Schull; Nylon membrane, pore size 0.2 μm, Osmonics; Nylon membrane, pore size 1.2 μm, Osmonics; and FTA-glass, grade F572-08, Whatman (used for comparison).

The Membranes were soaked with the FTA solution for two hours at room temperature with gentle agitation, dried completely at room temperature, and baked at 80° C. for one hour.

WBC Samples

Samples of various concentrations were used in the experiment. These concentrations include: WBC, 5×10³ cell/μl; WBC, 5 cell/μl; DNA-positive control, 2 μg/μl single stranded DNA in water, and WBC-negative control, 3% BSA in PBS.

Protocol

All assay steps were performed in one 96 well plate. The circles of each membrane, 0.5 mm in diameter, were put on the bottom of each well. WBC samples of 3 μl were loaded in each well, in duplicate. Then the plate was subsequently blocked with PBS/BSA/Twin-20 solution, incubated with Polyethyleneimine-Peroxidaze conjugate, washed with PBS/BSA/Twin-20 solution, and finally incubated with different substrates for Peroxidase to develop colored soluble or insoluble products.

Results

WBC positive and WBC-negative samples developed different color intensities on the FTA-nylon, and FTA-nitrocellulose membranes, each having a pore size of 0.2 μm. The color intensity developed when the result of the enzyme reaction was soluble product.

DNA positive and DNA-negative samples developed different color intensity in the FTA-nitrocellulose membrane, having a pore size of 0.2 μm. Again, the color intensity developed when the result of the enzyme reaction was insoluble product.

Conclusions

The color intensity developed on the FTA membranes in 96 well plate as a result of the PEI-PO assay. This directly correlates with the amount of WBC. The DNA can be released from WBC on FTA treated membrane for subsequent analytical determination.

Physical and chemical properties of the FTA-treated membrane such as pore size are important for DNA evaluation. On the basis of two experiments it has been shown that the membrane with a 0.8 μm pore size is the best for DNA determination, while 0.1 μm pore size membrane is more promising for WBC evaluation.

Results Presented in the 2 Tables and 2 Pictures, Marked as Following

| Rows: | | | | |
|---|---|---|---|---|
| I | | 0.2 μm nylon membrane | | |
| II | | 1.2 μm nylon membrane | | |
| III | | FTA-glass paper | | |
| IV | | 0.2 μm nitrocellulose | | |
| Columns: | A | B | C | D |
| Concentration | 5 × 10³ WBC/μl | 5 WBC/μl | 2 μg/μg DNA | 0-control |

Notice that 3 μl of the sample was loaded in the well.

Advantages include alleviating the bottleneck of nucleic acid preparation. Also, GC adapters on gene specific primers enable immobilization to the solid phase (See Yang et al. (1998) PNAS. Vol. 95, pp. 5462–5467). Additionally, DNA can be loaded on the FTA treated membrane for following ELISA determination and DNA can be released from WBC on FTA treated membrane (0.2 μm pore size) for following analytical determination.

Example 4

The detection limit of the PEI-PO assay on FTA cellulose nitrate membrane for single- and double-stranded DNA was analyzed.

Objectives:

Whatman Cellulose Nitrate membrane, pore size 0.8 μm was treated with FTA solution. Seven different variables were studied to find out the sensitive points of each step of the PEI-PO assay for DNA determination in 96 well plate and used to determine the detection limit of the method for purified DNA. DNA samples as single- and double-stranded DNA solutions were fixed on the FTA treated membranes in a 96 well plate, 40 pg–400 ng DNA/well. All steps and ingredients of the assay, plate pretreatment, baking step after loading DNA, blocking buffer, can contribute to the assay sensitivity. Preliminary results suggested that detection limit of this method on cellulose nitrate membrane pore size 0.8 is 40 pg/Nell for single-stranded DNA and 400 pg for double-stranded DNA.

Materials

Membranes:

Cellulose Nitrate Membranes were obtained from the Arbor Technologies samples library. Membranes having a pore size of 0.8 μm were utilized for the following experiments. The membranes were soaked with the FTA for one hour at 80° C., dried completely at room temperature, and baked at 80° C. for one hour.

DNA Samples:

Single-stranded human genomic DNA having the following concentrations were used: 20 ng/μl, 2 ng/μl, 200 pg/μl, 20 pg/μl. DEPC water was used as DNA-negative control. 2 μl of each DNA concentration sample was loaded onto the pieces of FTA cellulose nitrate membrane. The specimens were loaded in duplicate or triplicate.

Block solutions of PBS, 3% BSA, 0.1% Tween-20 (block solution #1), PBS, 3% BSA (block solution #2), and 10×Denhardt's solution (1% Ficoll 400, 1% polyvinylpyrolidone, 1% BSA), 4×SET (NaCl, EDTA, Tris-HCl, pH 8.0), 0.1% SDS (block solution #3) were used when conducting these experiments.

All of these this variables were chosen to find out the sensitive points of each step of the PEI-PO assay for DNA determination in 96 well plate.

Two experiments were performed with FTA cellulose nitrate membrane for DNA determination. The goal of the first experiment was to find the detection limit of the method for double and single stranded DNA using following protocol. First 2 µl of the different DNA solutions were fixed on the pieces of the membrane in 96 well plate in duplicate. The plate was baked for one hour at 80° C. Then, the plate was blocked with block solution 1 for one hour at 37° C. The plate was incubated with PEI-PO conjugate for one hour at 37° C., then washed three times with PBS, 0.1% Tween, for ten minutes at 37° C. The DNA in one set of the wells was visualized directly on the membrane when insoluble product of PO was developed after incubation with 3,3'-dianisidine. A duplicate set of the wells was incubated with 1,2-ortophenylenediamine dihydrochloride (OPD) and color development in supernatant was estimated at 490 nm.

The goal of the second experiment was to repeat the determination of the detection limit and compare the results after incubating plates with different block solutions. In this experiment, untreated plates and plates treated with 0.1% tween-20 were used. The membrane in each kind of plate, after DNA loading was either baked or not baked.

Results

The combination of washing the plate with tween-20 and using block solution #1 gave the best result with a low nonspecific background. The background measurement at 490 nm was as low as 0.200 on DNA negative membranes. Block solutions #2 and #3 increased nonspecific sorption of PEI-PO. The background measurement at 490 nm was 0.6–0.8. The detection limit of the method was found 40 pg/well for single-stranded DNA and 400 pg/well for double-stranded DNA. Baking step was find necessary for pure DNA determination by PRI-PO assay on the cellulose nitrate membrane.

Conclusions

The plate should be pretreated with 0.1% Tween-20 solution before DNA determination on the FTA membrane to create low nonspecific background. Among the three buffers only block solution #1 (PBS, 3% BSA, 0.1% Tween-20) works as a block solution for PEI-PO nonspecific sorption on the FTA-membrane.

Results suggested that the detection limit of this method on cellulose nitrate membrane having a pore size of 0.8 is 40 pg/well for single-stranded DNA and 400 pg for double-stranded DNA.

Example 5

Two ELISA modifications were used to confirm that DNA can be released from white blood cells (WBC) on an FTA treated cellulose nitrate membrane for subsequent quantitative determination.

Whatman Cellulose Nitrate and Nylon membranes, having a pore size of 0.2 µm, were treated with FTA solution. Two version of FTA treatment were used. First, membranes were treated with FTA in 96 well plate, and used for DNA determination in the same plate. Second, membranes were treated with FTA solution, dried, cut into the pieces, loaded into the plate and then used for DNA determination.

Two ELISA modifications were used to confirm, that DNA can be released from white blood cells (WBC) on FTA treated cellulose nitrate membrane for subsequent analytical determination.

Materials

Membranes

Whatman Cellulose Nitrate membranes, pore size 0.2, 0.8 µm and Whatman Nylon membranes, standard and SP, both with pore size of 0.2 µm were utilized.

FTA Treatment

Two treatments were applied: First—the pieces of the membranes, 5×10 cm, were soaked with the FTA solution (without uric acid) for 15 minutes, then baked at 80° C. for one hour. Second—membranes were stored between plain paper in plastic bags. Membranes were cut into circles of 0.5 mm diameter, and loaded into the 96 well plates. 10 µl of FTA solution was applied to each well on top of the membrane. The plate was completely dried at 80° C.

DNA Samples

Single-stranded human genomic DNA, of the following concentrations were used: 2 ng/µl, 200 pg/µl, 20 pg/µl; as well as DEPC water which was used as a DNA-negative control.

WBC Samples

WBC were isolated from fresh human blood after lysis of the red cells with ammonium chloride buffer and three washing steps with PBS, 1.5% BSA. WBC suspension was diluted to cell concentrations of $6 \times 10^3$, $4 \times 10^2$ and 2 cells per µl. 2 µl of each WBC concentration samples were loaded on the pieces of FTA membranes in duplicate or triplicate.

Study Design and Method

The goal of the experiments was to find the optimal FTA treatment of the membranes for DNA determination in a 96 well plate. The goal of the second experiment was to compare two different ELISA assays for WBC determination on the cellulose nitrate and nylon membranes.

ELISA was conducted on the basis of antibodies to human DNA and was designed after the optimization of all of the following steps: The experiment began with the loading of WBC and DNA samples on the pieces of FTA membranes in a 96 well plate. Then the plate was baked for one hour at 80° C. Incubation occurred next with block solution, PBS, 3% BSA, 0.1% Tween-20. Then there was incubation with human monoclonal antibodies (Abs) specific to human DNA, including 1 ug of Abs/ml for one hour at 37° C. or overnight in refrigerator. Subsequently, washing occurred three times for five minutes at room temperature. Incubation with mouse antibodies specific to human IgG conjugated with biotin, at a dilution of 1:15.000 occurred for one hour at 37° C. Then it was washed three times for five minutes at room temperature. Next, incubation with avidin-poly-HRP, at a dilution 1:5.000 occurred for 45 minutes at 37° C. Then it was washed three times for five minutes at room temperature. The OPD substrate was incubated for 20 minutes at 37° C. Incubation was stopped with 3M sulfuric acid. The supernatant was transferred from the wells to the replica plates. Then the reading plate was analyzed at 490 nm.

Results

A very high positive background developed on all membranes treated with FTA in the plate. No statistical differences were observed between DNA-positive and DNA-negative wells with membranes, which were treated with FTA in the plate. When the membranes were treated with FTA before loading in the plate, very bright dark brown rings were formed on the cellulose nitrate membranes loaded with WBC, $8 \times 10^3$ cell per µl during PEI-PO assay. The same bright rings for this WBC concentration, as well as for the concentration of $40 \times 10^2$, were observed on the cellulose nitrate membrane with an assay based on antibodies to human DNA. No rings were seen on the membranes loaded with pure DNA, or 20 WBC for µl samples. The color intensity measured in the plates after PEI-PO and antibodies to human DNA assays at 490 nm presented in the following table.

Color Intensity Developed on the WBC Samples Loaded on the FTA-Cellulose Nitrate Membrane ELISA Assays, Reading at 490 nm, March 10–14 Tests

|  | PEI-PO Assay | | Abs to human DNA | |
| --- | --- | --- | --- | --- |
|  | Mean | SD | Mean | SD |
| 8 × 10³ cell/µl | 1.491 | 0.152 | 2.013 | 0.771 |
| 4 × 10² cell/µl | 1.255 | 0.214 | 0.645 | 0.104 |
| 20 cell/µl | 1.079 | 0.204 | 0.303 | 0.041 |
| DNA-positive control | 1.120 | 0.290 | 0.405 | 0.026 |
| DNA-negative control | 0.830 | 0.117 | 0.324 | 0.042 |

The color intensity developed on WBC positive membranes directly depends on WBC concentration. Nonspecific background was lower after an assay based on antibodies to human DNA. Both assays gave similar intensity between DNA positive and DNA negative samples, 0.74 for PEI-PO assay and 0.8 for antibodies to human DNA assay. But in the case of using specific antibodies, a more pronounced difference was observed between samples with different WBC concentration.

Conclusions

DNA can be released from WBC on FTA treated cellulose nitrate membranes for subsequent determination. Color intensity developed on the WBC positive membranes depends on cell concentration.

Immunoassays based on the interaction between DNA and polyethyleneimine (nonspecific) or DNA and monoclonal antibodies to DNA (specific) can be applied to DNA determination on FTA cellulose nitrate membranes in a 96 well plate. Treatment of the membrane with FTA directly in the wells of the plate results in a very high non-specific sorption of PEI to the membrane.

Nylon membranes, both standard and SP, having pore sizes of 0.2, have a very high nonspecific background after incubation with PEI-PO and antibodies to human DNA assays. In the present setting, these membranes could not be recommended for DNA determination with ELISA assays.

Example 6

FTA Nitro Cellulose membrane application for measurement of the level of antibodies to human DNA. Lupus disease diagnostics.

Study Design:

Double stranded genomic DNA or suspension of WBC as sources of human DNA was loaded on the pieces of FTA-nitro cellulose membrane in 96 well plate. Plate was incubated with antibodies (Abs) specific to human DNA, which were obtained from the patient with Lupus disease. Concentration of Abs was 1 µg of Abs/ml. ELISA assay on the basis of mouse anti-human Abs conjugated with biotin and poly-avidin-HRP were performed on the plate. The color intensity developed in the Abs to human DNA positive wells and control wells measured at 490 hm.

Results

Color Intensity Developed on the FTA-cellulose Nitrate Membrane in Abs to Human DNA Positive Wells by ELISA Assays, Reading at 490 nm

|  | Abs to Human DNA | Control |
| --- | --- | --- |
| WBC as DNA source | 2.013 +/− 0.777 | 0.324 +/− 0.042 |
| Genomic DNA as DNA source | 0.405 +/− 0.026 | 0.324 +/− 0.042 |

Conclusion

FTA-treated membrane can be used to load DNA for following determination of antibodies specific to human DNA in the plasma of patients with Lupus disease.

FTA coated filter materials are known to the art as tools for the analysis of genetic materials (Flinders Patents) particularly for genomic DNA from any number of sources. Nucleic acid from blood samples can be purified, retained, and readily utilized for PCR on FTA coated material such as cellulosic 3IET or glass microfiber. The genetic material bound to FTA filters can be stored in a useable state at room temperature for a great deal of time (up to 10 years to date).

There are many ways that FTA coated materials can be utilized to address the concerns listed previously. Such utilization would include:

1. FTA Tags Attached to Donated Blood Bags.

A blood spot from the donor administered to an FTA card attached to a blood bag into which the donor is contributing would solve problems such as traceability, archiving safety (pathogens are completely inactivated on FTA) of handling. One would not need to draw blood from the bag for NAT, thereby negating the need for elaborate QC measures to prevent cross-contamination of neighboring blood samples.

2. FTA Provides a Rapid Method for Nucleic Acid Purification.

Currently in the blood transfusion community, nucleic acid from donated samples is prepared by traditional techniques which take up to 90+ minutes. Preparation of usable nucleic acid when using FTA material takes ten minutes. Materials such as a 96 well microplate or tube containing FTA filters could be utilized by blood services for rapid preparation. There is also provision to include the technique of eluting nucleic acid from the FTA filter if a soluble fraction may be more useful for some of the pathogen detection systems such as transcription mediated amplification (TMA).

3. 96 Pooled Samples.

A 96 well microplate containing FTA filter material could be used to provide longer pool analysis than that which is currently undertaken (24 is normal). The advantage of a 96 well FTA tool is that all samples are processed as one, but yield singular results, completely negating the need for iterative analysis if the traditional pool is found as pathogen-positive. There would also be a reduced risk for 'false-positive' results that occur by inadvertently following the wrong iterative pathway.

4. Blood Archive Cards.

An extension of the blood bag tag idea where a portion of the original tag is archived for 'look back' purposes as new pathogens are discovered and become of interest. FTA solid phase storage of nucleic acid has been shown to yield usable product after ten years of RT storage. Storage/archive could be carried out in a file cabinet instead of frozen aliquots.

5. NAT Prior to Blood Donation.

Administer a drop of blood (donor) to a card provided (or brought in by donor). Test by NAT, and if clear, draw donated blood after this testing. The advantage being that only safe blood enters the community.

6. Multiple Pathogen Testing.

Donor blood administered to an FTA device can be tested for many pathogens at once by PCR techniques. A 50 $\mu$l blood spot yields a large surface on a filter from which many one millimeter punches can be taken. Also, the provision exists to carry out different, specific PCR reactions on the same punch.

7. Transport of Blood Sample.

Donations taken at institutions do not necessarily carry out NAT. Expensive measures are taken to draw blood into tubes and them ship them to NAT testing centers. An FTA device with a donor blood spot can be sent via US postal service at room temperature with no additional expense.

8. Ambulance FTA Cards.

Accident victims, etc. can be NAT tested very rapidly if victim blood is archived to an FTA card that is carried by the ambulance crew.

Example 7

The following experiment demonstrates that DNA or genetic material isolated from low amounts of white blood cells, such as 33 cells per well or 0.33 cell/$\mu$l, can be measured.

White blood cell concentration of 1 cell per microliter ($\mu$l) represents the amount of cells allowed for a whole blood unit, having a volume of 500 ml, to be marked as leukoreduced (LR) according to the European Standard. This method is able to detect such low levels of concentration that it can be recommended for QC of leukoreduced blood.

Materials and Protocol:

White blood cell suspensions were obtained from whole blood samples after lysing red blood cells with ammonium chloride buffer. The concentration of white blood cells can be in the range of 1 to 1000 cells per $\mu$l. In this experiment, 100 $\mu$l of white blood cells from leukoreduced blood was loaded on FTA membrane and resulted in the collection of 600 pg DNA per well (note that there are 6 pg of DNA in a single human cell). Fluorescent stain of cell nucleus with Propidium Iodine detergent solution and fluorescent microscopy were used for validation of white blood cell lysis on the FTA membrane.

A 96 well plate with control nitrocellulose membrane and the FTA membrane were loaded with white blood cells. Two methods were used. At first, the white blood cell suspension was spotted on the membrane in a volume of 2.5 $\mu$l/well. According to a second protocol, different volumes of white blood cells in the range of 20–180 $\mu$l/well were applied to the membrane by vacuum filtration. Two different ELISA systems were used to measure DNA in each well. The first ELISA was based on polyethyleneimine-peroxidase conjugate. The second protocol used monoclonal antibodies specific to human genomic DNA.

The detection limit was achieved by conducting an experiment when the same plate was loaded with genomic DNA samples in concentration range of 0.2–20 ng per well and white blood cell samples in amount of 90–360 per well. DNA samples were spotted on the membrane in volume of 2 $\mu$l per well. White blood cell samples were loaded in volumes of 30–120 $\mu$l per well by vacuum filtration.

Results:

The white blood cells stained with Propidium Iodine and spotted on nitrocellulose membrane can be observed with a fluorescent microscope which are seen as bright pink spots spread over the membrane surface. The amount of cells counted on the membrane depends on the amount of white blood cells loaded. Propidium Iodine staining indicated that no intact cells remained on the FTA membrane spotted with the same amount of white blood cells. The color intensity of the ELISA product developed on the FTA membrane has a linear correlation with the amount of white blood cells loaded per well. The detection limit for white blood cell was determined to be 100 cells per well. This represents the concentration of 1 cell/$\mu$l. The volume capacity was found as 100 $\mu$l of white blood cells suspension per well. When 3'3-diaminobenzidine was used as substrate for peroxidase, an insoluble product formed in the white blood cell positive wells as brown rings on the FTA membrane. The thickness and intensity of thee rings depends on the amount of cells in the well.

The volume capacity for 0.8–1.2 FTA-NC membrane was shown to be ~100 $\mu$l of white blood cell suspension per well. So, it is possible to obtain 600 pg of DNA per well. This amount can be detected on FTA-NC membranes with ELISA using antibodies specific to human DNA above the background.

The sensitivity of the method, which causes the FTA membrane to lyse cells and capture of cell DNA and ELISA detection system on the basis of antibodies specific to human DNA is 0.2 ng of DNA per well in a 96 well plate format. In the initial experiments the sensitivity of the method was found as ~100 $\mu$l per well of white blood cell suspension with cell concentration of 3 cells per $\mu$l (as average count), or 5+/−4 cells/$\mu$l. Accuracy at this level is in the range of 5+/−4 cells per $\mu$l. However, in an additional experiment, using the same method, the sensitivity was determined to be 33 cells per well.

Figure 5:
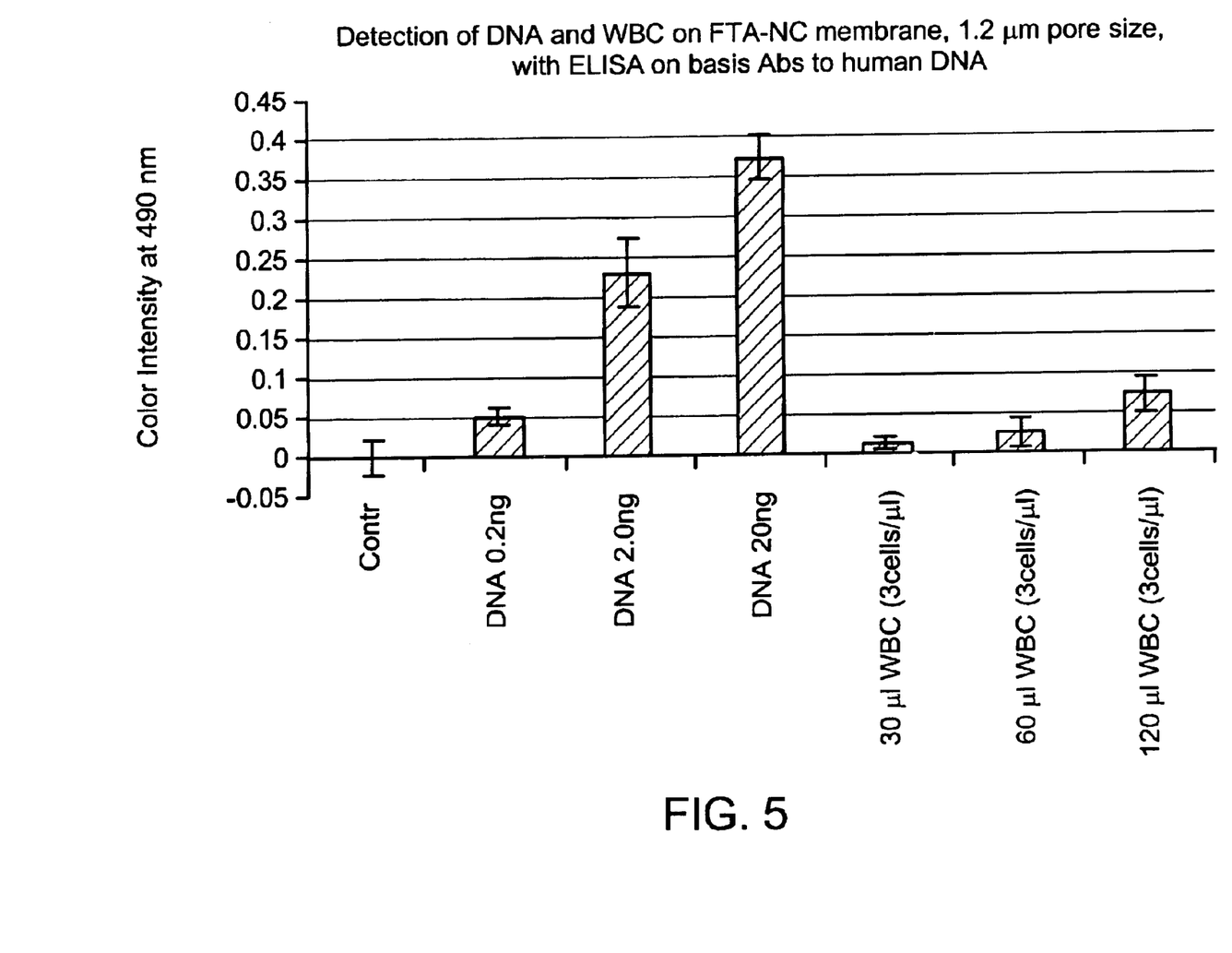
FIG. 5 is a graph showing the detection of DNA and white blood cells on FTA-NC membranes having a 1.2 $\mu$m pore size using ELISA on the basis of antibodies to human DNA.

With ELISA, on the basis of antibodies specific to human DNA, it was possible to see a difference between control wells loaded with PBS and DNA and white blood cell positive wells loaded with 0.2 ng DNA/well or 60 $\mu$l white blood cells/well. There is a linear dependency between color intensity of the assay and the amount of DNA. Additionally, there is a linear dependency between the assay and the white blood cells loaded per well. The data is presented in FIG. 5.

Sensitivity of ELISA on the Basis of Antibodies to Human DNA for DNA Determination and Determination of White Blood Cells on FTA Membranes

| Control | DNA 0.2 ng | DNA 2.0 ng | DNA 20 ng | 30 mkl WBC (3 cells/$\mu$l) | 60 mkl WBC (3 cells/$\mu$l) | 120 mkl WBC (3 cells/$\mu$l) |
|---|---|---|---|---|---|---|
| 0 | 0.05 | 0.23 | 0.373 | 0.01 | 0.02 | 0.07 |
| 0.02 | 0.01 | 0.04 | 0.03 | 0.01 | 0.02 | 0.02 |

Conclusions:

The experiment demonstrates that FTA membrane can be used for white blood cell membrane lysis, cellular DNA capture, and quantitative determination with ELISA. The method illustrates that DNA isolated from low amounts of white blood cells, such as 33 cells per well or 0.33 cell/$\mu$l, can be measured above the background. This technique has wide application for counting low amounts of cells in a variety of liquids.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

GC adapter immobilization to cellulose—Public domain; Yang et al. (1998) PNAS. Vol. 95. pp. 5462–5467.
Flinders University FTA prior art
Whatman FTA Elute—Patent Pending
Organon Tachnicka—PAM Technology
GeneTrace—Solid Phase Hybrid Capture (Ligation detection)
U.S. Pat. No. 5,496,562, Solid Medium and Method for DNA Storage, 1996
Renz, m., C. Kurz, "A calorimetric method for DNA hybridization", Nucleic Acids Research, 1984, v. 12, No. 8, p. 3435–3444
Matsuhisa A., Y Kish, K Shiba, "A Simple Staining Method for DNA and RNA blotted on a Membrane Using a Polyethyleneimine-Enzyme Conjugate", J. Biochem., 1994, v. 116, p. 478–481

What is claimed is:

1. A method of purifying nucleic acid comprising the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a sample comprising nucleic acid;
   c. capturing the nucleic acid with the substrate;
   d. optionally, fixing the nucleic acid to the substrate;
   e. treating the nucleic acid on the substrate with an external substance which generates a signal in an assay, wherein the external substance comprises polyethyleneimine; and
   f. generating a signal to indicate the presence of the nucleic acid.

2. A method of purifying nucleic acid comprising the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a sample comprising nucleic acid;
   c. capturing the nucleic acid with the substrate;
   d. optionally, fixing the nucleic acid to the substrate;
   e. treating the nucleic acid on the substrate with an external substance which generates a signal in an assay, wherein the assay comprises an enzyme-linked immunosorbant assay (ELISA); and
   f. generating a signal to indicate the presence of the nucleic acid.

3. A method of purifying nucleic acid comprising the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a sample comprising nucleic acid;
   c. capturing the nucleic acid with the substrate;
   d. optionally, fixing the nucleic acid to the substrate, wherein the fixing of the nucleic acid to the substrate comprises heating the substrate with the captured nucleic acid;
   e. treating the nucleic acid on the substrate with an external substance which generates a signal in an assay; and
   f. generating a signal to indicate the presence of the nucleic acid.

4. A method of purifying and analyzing DNA in a blood sample, wherein the method comprises the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a blood sample comprising DNA;
   c. capturing the DNA with the substrate;
   d. optionally, fixing the DNA to the substrate;
   e. treating the DNA which is maintained on the substrate with an external substance which generates a signal in an assay;
   f. generating a signal to indicate the presence of DNA captured and maintained on the substrate;
   g. analyzing the amount of DNA captured and maintained on the substrate by quantifying the generated signal; and
   h. analyzing the number of leukocytes in the blood sample by the amount of captured DNA analyzed by quantifying the generated signal.

5. A method of purifying and analyzing DNA in a blood sample, wherein the method comprises the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a blood sample comprising DNA;
   c. capturing the DNA with the substrate;
   d. optionally, fixing the DNA to the substrate;
   e. treating the DNA on the substrate with an external substance which generates a signal in an assay, wherein the external substance comprises polyethyleneimine;
   f. generating a signal to indicate the presence of DNA; and
   g. analyzing the amount of DNA captured the substrate by quantifying the generated signal.

6. A method of purifying and analyzing DNA in a blood sample, wherein the method comprises the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a blood sample comprising DNA;
   c. capturing the DNA with the substrate;
   d. optionally, fixing the DNA to the substrate;
   e. treating the DNA on the substrate with an external substance which generates a signal in an assay, wherein the assay comprises an enzyme-linked immunosorbant assay (ELISA);
   f. generating a signal to indicate the presence of DNA; and
   g. analyzing the amount of DNA captured by quantifying the generated signal.

7. A method of purifying and analyzing DNA in a blood sample, wherein the method comprises the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a blood sample comprising DNA;
   c. capturing the DNA with the substrate;
   d. optionally, fixing the DNA to the substrate, wherein the fixing of the DNA to the substrate comprises heating the substrate with the captured DNA;
   e. treating the DNA on the substrate with an external substance which generates a signal in an assay;
   f. generating a signal to indicate the presence of DNA; and
   g. analyzing the amount of DNA captured by quantifying the generated signal.

8. A method of purifying nucleic acid comprising the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a sample comprising nucleic acid;
   c. capturing the nucleic acid with the substrate;
   d. optionally, fixing the nucleic acid to the substrate;
   e. treating the nucleic acid which is maintained on the substrate with an external substance which generates a signal in an assay, wherein the external substance comprises polyethyleneimine; and
   f. generating a signal to indicate the presence of the nucleic acid which is maintained on the substrate.

9. A method of purifying nucleic acid comprising the steps of:
   a. providing a dry substrate comprising:
      i. a solid matrix, wherein the solid matrix comprises nitrocellulose or nylon; and
      ii. a coating, wherein the coating comprises an anionic surfactant or detergent which facilitates cellular lysis;
   b. applying to the substrate a sample comprising nucleic acid;
   c. capturing the nucleic acid with the substrate;
   d. optionally, fixing the nucleic acid to the substrate;
   e. treating the nucleic acid which is maintained on the substrate with an external substance which generates a signal in an assay, wherein the assay comprises an enzyme-linked immunosorbant assay (ELISA); and
   f. generating a signal to indicate the presence of the nucleic acid which is maintained on the substrate.

10. A method of purifying nucleic acid comprising the steps of:
    a. providing a dry substrate comprising:
       i. a solid matrix, wherein the solid matrix comprises nitrocellulose or nylon; and
       ii. a coating, wherein the coating comprises an anionic surfactant or detergent which facilitates cellular lysis;
    b. applying to the substrate a sample comprising nucleic acid;
    c. capturing the nucleic acid with the substrate;
    d. fixing the nucleic acid to the substrate wherein fixing comprises heating the substrate with the captured nucleic acid;
    e. treating the nucleic acid which is maintained on the substrate with an external substance which generates a signal in an assay; and
    f. generating a signal to indicate the presence of the nucleic acid which is maintained on the substrate.

11. A method of purifying and analyzing DNA in a blood sample, wherein the method comprises the steps of:
    a. providing a dry substrate comprising:
       i. a solid matrix, wherein the solid matrix comprises nitrocellulose or nylon; and
       ii. a coating, wherein the coating comprises anionic surfactant or detergent which facilitates cellular lysis;
    b. applying to the substrate a blood sample comprising DNA;
    c. capturing the DNA with the substrate;
    d. optionally, fixing the DNA to the substrate;
    e. treating the DNA which is maintained on the substrate with an external substance which generates a signal in an assay wherein the external substance comprises polyethyleneimine;
    f. generating a signal to indicate the presence of DNA captured and maintained on the substrate; and
    g. analyzing the amount of DNA captured and maintained on the substrate by quantifying the generated signal.

12. A method of purifying and analyzing DNA in a blood sample, wherein the method comprises the steps of:
    a. providing a dry substrate comprising:
       i. a solid matrix, wherein the solid matrix comprises nitrocellulose or nylon; and
       ii. a coating, wherein the coating comprises an anionic surfactant or detergent which facilitates cellular lysis;
    b. applying to the substrate a blood sample comprising DNA;
    c. capturing the DNA with the substrate;

d. optionally, fixing the DNA to the substrate;
e. treating the DNA which is maintained on the substrate with an external substance which generates a signal in an assay wherein the assay comprises an enzyme-linked immunosorbant assay (ELISA);
f. generating a signal to indicate the presence of DNA captured and maintained on the substrate; and
g. analyzing the amount of DNA captured and maintained on the substrate by quantifying the generated signal.

13. A method of purifying and analyzing DNA in a blood sample, wherein the method comprises the steps of:
a. providing a dry substrate comprising:
  i. a solid matrix, wherein the solid matrix comprises nitrocellulose or nylon; and
  ii. a coating, wherein the coating comprises an anionic surfactant or detergent which facilitates cellular lysis;
b. applying to the substrate a blood sample comprising DNA;
c. capturing the DNA with the substrate;
d. optionally, fixing the DNA to the substrate wherein fixing comprises heating the substrate with the captured nucleic acid;
e. treating the DNA which is maintained on the substrate with an external substance which generates a signal in an assay;
f. generating a signal to indicate the presence of DNA captured and maintained on the substrate; and
g. analyzing the amount of DNA captured and maintained on the substrate by quantifying the generated signal.

* * * * *